United States Patent [19]
Turyan et al.

[11] Patent Number: 5,773,295
[45] Date of Patent: Jun. 30, 1998

[54] DETERMINATION OF ACID VALUES IN OIL SEEDS

[76] Inventors: Yaakov I. Turyan, Neve Yaakov 425/12, Jerusalem 97350; Oleg Yu Berezin, st. Asher Golan 14/7, 97350 Jerusalem; Ilya Kuselman, Haim Pazner St. 29/5, Jerusalem 97552; Avinoam Shenhar, 4 Tiltan, Jerusalem 96926, all of Israel

[21] Appl. No.: 727,362

[22] Filed: Oct. 8, 1996

[30] Foreign Application Priority Data

Oct. 19, 1995 [IL] Israel ......................................... 115677

[51] Int. Cl.⁶ .................................................... G01N 33/02
[52] U.S. Cl. ................................ 436/20; 436/23; 436/60; 436/61; 436/71; 426/417
[58] Field of Search .................................. 436/20, 23, 60, 436/61, 71; 426/417

[56] References Cited

U.S. PATENT DOCUMENTS

| | | | |
|---|---|---|---|
| 3,615,226 | 10/1971 | Apter ..................................... | 23/230 R |
| 4,098,575 | 7/1978 | Matsushita ............................ | 23/230 R |
| 4,654,309 | 3/1987 | Mlinar et al. ............................. | 436/20 |
| 5,196,169 | 3/1993 | Schick et al. .............................. | 436/23 |
| 5,620,897 | 4/1997 | Zappe ........................................ | 436/23 |

FOREIGN PATENT DOCUMENTS 0151278  8/1985  European Pat. Off. ................. 436/61

OTHER PUBLICATIONS

Lapshina et al. "pH–metric determination of acid numbers for oils". Zh. Anal. Khim. (1991), 46 (6), 1150–8. Abstract only.

Danil'chuk et al. "Determination of the acid number of oils in sunflower seeds." Maslo–Zhir. Prom.-st. (1984), (6), 9–10 Abstract only.

Danil'chuk et al. "Accelerated method for the determination of the acid number of the oil in sunflower seeds". Maslo–Zhir. Prom.-st. (1979), (9), 6–8. Abstract only.

Turyan et al., Plenum Publishing Co., 1991, pH–Metric Method for the Determination of Acid Numbers of Oils, pp. 833–840, Translated from Zhurnal Analiticheskoi Khimii, vol. 46, pp. 1150–1158, Jun. 1991, Original in Russian.

May et al., An Automated Gas–Liquid Chromatographic Method of Measuring Free Fatty Acids on Canola, vol. 70, Mar. 1993, pp. 229–233.

International Standard, Oilseeds–Determination of Hexane Extract (or light petroleum extract), called "oil content", ISO 659: 1988(E), pp. 1–5.

*Primary Examiner*—Jill Warden
*Assistant Examiner*—Sharidan Carrillo
*Attorney, Agent, or Firm*—Evenson, McKeown, Edwards & Lenahan, P.L.L.C.

[57] ABSTRACT

A method for determining the acid value of oilseeds. A reagent kit for the rapid extraction of the free fatty acids from oilseeds which consists of reagents: "A" and "B". Reagent "A" contains a tertiary amine (such as triethanolamine) in water and an alcohol—hydrocarbon mixture as solvent. Preferred is water/isopropanol/heptane. Reagent "A" allows rapid (1–2 min) solid-liquid extraction of the free fatty acids and some other acids from oilseeds. Reagent "B" contains a strong acid and an inorganic salt in water. Reagent "B" enables the rextraction (liquid-liquid; about 5 min) of the free fatty acids only into a separate hydrocarbon phase, which can be used for the acid value determination.

9 Claims, No Drawings

DETERMINATION OF ACID VALUES IN OIL SEEDS

FIELD OF THE INVENTION

The invention refers to oilseed analysis, in particular to the determination of the total concentration of free fatty acids or acid value (AV) in oilseeds. The AV value is expressed by mg KOH necessary for titration of free fatty acids contained in 1 g oil in oilseeds. The AV is an important characteristic of oilseed quality.

A set of reagents for rapid and quantitative extraction of the free fatty acids from oilseeds is provided by in the invention. The AV value can be determined in the extract by one of known techniques (titration, pH-metry, chromatography and others). The set consists of two reagents: A and B. Reagent A provides for the rapid (1–2 min) and complete extraction of the free fatty acids and partial extraction of some other acids. Reagent B allows to separate the free fatty acids from others during about 5 minutes for the AV determination.

BACKGROUND OF THE INVENTION

The international standard (ISO 659, 1988-02-15) for AV determinations in oilseeds is based on the time-consuming (4 hours and more) extraction of the oil with the free fatty acids by hexane or light petroleum.

The reagent of T. M. Lapshina et al., Zh. Anal. Khim., 46 (1991) 1150 (80% diethyl ether+19% ethyl alcohol+1% water (vol) containing 0.15–0.20M triethanolamine-TEA), has allowed to decrease the extraction time.

However. the extract contained not only free fatty acids but other acids too (probably from proteins). Therefore, the analysis was carried out by limitation of the extraction to 1 minute in order to obtain the AV close to those of the standard method. But even within 1 minute the extraction of other acids by this technique was not completely eliminated. This fact can be a source of positive errors and/or insufficient reproducibility.

Other reagent in the technique-precursor used by W. E. May et al., JAOCS, 70 (1993) 229, consisted of 0.01M $H_2SO_4$ in the solvent 78% isopropanol+20% heptane+2% water, vol. After the extraction during 15 minutes heptane, water was added and the AV value was determined in the upper heptane layer. The authors cited, observed negative errors in results of the AV determination (from 4 up to 34 relative %).

Drawbacks of the known reagents are:

1. The reagent in the standard method (ISO 659, 1988-02-15) requires long time for the extraction (4 hours and more).

2. The reagent of T. M. Lapshina et al. (Zh. Anal. Khim.,46 (1991) 1150) can not guarantee selective and reproducible extraction of free fatty acids.

3. The reagent of W. E. May et al. (JAOCS, 70 (1993) 229) leads to incomplete extraction of the free fatty acids. The aim of the present invention was to develop reagents free from the indicated drawbacks.

SUMMARY OF THE INVENTION

The present invention relates to a method for the determination of acid value of oilseeds which comprises:

drying comminuted oilseeds, introducing the comminuted oil-seed sample into Reagent A comprising a tertiary amine, water, an alcohol and a hydrocarbon; and agitating this mixture for a few minutes;

adding to the mixture Reagent B, which comprises a strong acid and a salt in water; and agitating the mixture; thus taking up the free fatty acids into the upper hydrocarbon phase, removing an aliquot from the upper phase and determining the acid value by conventional means in said aliquot.

The invention relates to a set of reagents for rapid free fatty acids extraction from oilseed for the assay of the acid value which consists of two reagents: A and B, where preferably Reagent A comprises a tertiary amine in a mixture of water, and alcohol and hydrocarbon, where the alcohol is isopropanol at concentrations from 50 to 65% (vol.), where the hydrocarbon is heptane with concentration from about 28 to 48% (vol.), where the amine is triethanolamine at concentrations from about 0.05 to 0.15M, where Reagent B comprises a strong acid and an inorganic salt in water, which strong acid is preferably $H_2SO_4$ with concentrations from about 0.5 to 2.5M and where the inorganic salt is $Na_2SO_4$ at concentrations from about 1.3 to 1.5M.

The Reagents

The set of reagents according to the invention consists of two reagents:

reagent A and reagent B. Reagent A is a one-phase system containing 0.05–0.15M TEA in the solvent: 50–65% isopropanol+28–48% heptan+1–7% water (vol.). Reagent B consists of 0.5–2.5M $H_2SO_4$+1.3–1.5M $Na_2SO_4$ in water.

TEA in reagent A accelerates the extraction of acids. The complete extraction of the free fatty acids (with partial extraction of other acids) into reagent A is carried out during 1–2 minutes. Only in some cases, for example for Soya bean and Canola seeds, the extraction into reagent A is sufficiently rapid (1–2 min) without TEA. Since reagent A extracts from oilseeds also other acids, after the extraction (solid-liquid) reagent B is added to the system for reextraction (liquid-liquid) of the free fatty acids only.

Comparing the technique-precursor (W. E. May et al., JAOCS, 70 (1993) 229) one can see that their first reagent was acid, but our reagent A is basic or neutral. The phase separation in the precursor was performed by heptane and water, and in our technique—by the reagent B includes an acid and an inorganic salt. There are also different number of phases at the completion of the reextraction. The system formed by the technique-precursor consists of two phases: the lower isopropanol+water phase and the upper heptane phase. according to this invention there are three phases: the lower water+salt phase, the middle isopropanol phase and the upper heptane phase.

The different number of phases and their nature have principal significance since in case of the three-phase system (our invention) the solid material of oilseeds after the reextraction is localized on the boundary between the lower and middle phases and this improves essentially the separation of the upper heptane phase used for the AV determination.

The presence of the salt $Na_2SO_4$ causes the formation of three phases, and the high concentration of $H_2SO_4$ (in comparison with technique-precursor) leads to the complete reextraction of the free fatty acids into the upper heptane phase. At a $Na_2SO_4$ concentration in the reagent B of 1.3–1.5M the volume of the upper phase equals that of the initial heptane volume. If acid concentration is less than 0.5M, the reextraction of the free fatty acids is incomplete, and if higher than 2.5M, the obtained AV values are larger than those determined by the standard method, probably because of hydrolysis of triglycerides.

The Use Of The New Reagents For Av Determination In Oilseeds

An exact quantity (2–5 g) of ground and dried oilseeds is introduced into a Nessler cylinder, 35 ml of reagent A are added, the cylinder is closed and shaken during 1–2 min. Then 15 ml of reagent B are added and shaken. The cylinder is left during ~5 min with turning periodically for better phase separation. The upper phase is removed from the cylinder and treated with dry sodium or magnesium sulfate for rapid elimination of an eventual opalescence. An aliquot is taken for the AV determination by the pH-metric method (Ya. I. Tur'yan, O. Yu. Berezin, I. Kuselman and A. Shenhar, Pat. Israel, Appl. 110192, 01.07.94) or by the titrimetric method (ISO 660-1983 (E)), or another.

EXAMPLES

Acid Values (AV) of commercial oilseeds such as Sunflower, Soya and Canola were determined. For comparison AV values in the samples of oilseeds were determined first by the standard technique (ISO 659,1988-02-15). The samples of oilseeds were ground in a coffee grinder. A weighed sample of meal was placed into a thimble, extracted by n-hexane in a Soxhlet apparatus for 4 hours. The solvent was eliminated in a vacuum rotor evaporator for 1 hour. The weight of the extract served for the determination of the oil content in seeds. AV of the extracted oil was determined by titration in accordance with the standard technique (ISO 660-1983(E)). The results obtained by this way are shown in the Table.

Identical oilseed samples were used for AV determination by the novel extraction technique. After extraction AV was determined by analysis of the upper heptane layer either by pH-metric technique (Pat. Israel, Appl. 110192, 01.07.94) or by non-aqueous titration (ISO 660-1983 (E)).

Example 1

AV Determination in Sunflower Seeds

Oil content in Sunflower oilseeds used for analysis was P=51.9%. A sample of ground seeds, 3.738 g were placed into a Nessler cylinder. Reagent A, 35 ml were added into the cylinder. The closed tube was vigorously shaken for 1 minute. Then 15 ml of reagent B were added into the cylinder. The cylinder was again vigorously shaken and left for 5 minutes. The upper phase was removed with a pipette and placed into a test tube and a small amount of dry $Na_2SO_4$ was added to the tube.

AV was determined by pH-metric technique. To 50 ml of the reagent (0.2M TEA in solution isopropanol: water=1:1 with $pH'_0$=11.35) 8 ml of upper phase were added; stable pH-value was measured: $pH'_1$=10.27; then 0.4 ml of 0.1 N HCl (standard addition) was added to the solution and pH was measured again: $pH'_2$=9.94. AV was calculated using the equation $$AV = 56.11 V_{HCl} N_{HCl} V_o 100 / GV[10^{(pH'_1 - pH'_2)} - 1]P, \quad (1)$$

where 56.11 is the molecular mass of KOH;

$V_{HCl}$ is the volume of the standard addition of HCl, in the example $V_{HCl}$=0.4 ml;

$N_{HCl}$ is concentration of HCl, in the example $N_{HCl}$=0.1M;

$V_0$ is volume of the upper heptane layer, $V_0$=15 ml;

G is weight of the oilseed sample, g;

P is oil content, %;

V is aliquot of the upper heptane layer for analysis, ml.

The result of calculation was AV=1.90 mg KOH/1 g oil.

Example 2

AV Determination in Soya Bean

Oil content in Soya bean used for analysis was P=18.9%. A sample of Soya bean, 4.009 g were placed into a Nessler cylinder. The extraction of free fatty acids and isolation of upper heptane layer were the same as in example 1. AV determination in this case was made also by the pH-metric technique. For aliquot of upper phase 8 ml $pH'_1$=10.64 was measured, and after standard addition of 0.2 ml 0.1M HCl–$pH'_2$ =10.29. AV was calculated in according with formula (1). The result of calculation was AV=1.93 mg KOH/1 g oil.

Example 3

AV Determination in Canola Seeds

Oil content in Canola seeds used for analysis was P=41.5%. The sample of ground oilseeds, 4.112 g were placed into a Nessler cylinder. Extraction of free fatty acids, isolation of upper phase were the same as in example 1. Analysis of AV in upper phase was performed by non-aqueous titration. An aliquot V=5 ml of the upper phase were added to 40 ml of neutralized mixture ethyl alcohol: diethyl ether=1:1 and titrated by alcoholic KOH solution ($N_{KOH}$=0.0284M) in the presence of phenolphthalein. AV was calculated using the formula $$AV = 56.11 V_{KOH} N_{KOH} V_0 100 / G \, V \, P, \quad (2)$$

where $V_{KOH}$=0.94 ml is volume of KOH solution which was used for the neutralization of free fatty acids. The result of calculation was AV=2.42 mg KOH/1 g oil.

PRECISION AND ACCURACY OF AV DETERMINATIONS

Precision and accuracy of the results of AV determinations with the use of the novel reagents are similar to those for the standard technique (ISO 659, 1988-02-15; 660-1983 (E)).

In the Table there are shown the average results obtained by standard and novel techniques from n=5 replicates (parallel determinations) for each, $AV_s$ and $AV_p$ respectively; standard deviations of these replicates, $S_s$ and $S_p$ respectively; F-ratio $F = S_p^2 / S_s^2$ and t-ratio $t = (AV_s - AV_p) / [(S_s^2 + S_p^2)/5]^{0.5}$. The details of experiments are described above (see "Examples").

Table

Comparison of results of the AV determination (mg KOH/1 g oil) by the standard technique and by the novel technique

| Oil seeds | $AV_p$ | Sp | AVs | Ss | F | t |
|---|---|---|---|---|---|---|
| Sunflower | 1.66 | 0.21 | 1.69 | 0.19 | 1.21 | 0.30 |
| Soya | 1.97 | 0.07 | 2.06 | 0.15 | 2.00 | 1.16 |
| Canola | 2.67 | 0.07 | 2.60 | 0.13 | 1.87 | 1.13 |

The critical value for F-ratio is 6.39 at the 5% level of confidence and the number of degrees of freedom n−1=4. For t-ratio the critical value is 2.31 at the 5% level of confidence and 2(n−1)=8 degrees of freedom. From comparison of the F-data with the critical value it follows that difference between precision of results obtained by standard and proposed techniques is insignificant (all F values are less than the critical one). The accuracy for these techniques is approximately the same so far as the deviations of the average results obtained by proposed technique ($AV_p$) from the average results obtained by the standard technique ($AV_s$) are insignificant in comparison with the random errors: all t values are less than 2.31.

ADVANTAGES OF THE NOVEL REAGENT AND ITS USE

The main advantages of the suggested set of reagents for free fatty acids extraction from oilseeds with purpose of the AV determination consist in short extraction time (up to ~10 min) maintaining the accuracy and reproducibility of the AV determination on the required level.

We claim:

1. A method for determination of an acid value of an oilseed which comprises:
    a) drying a comminuted sample of said oilseed;
    b) introducing the comminuted oilseed sample into a Reagent A comprising a tertiary amine, water, an alcohol, and a hydrocarbon to form a first mixture and agitating said first mixture for a predetermined time period to thereby first extract free fatty acids and other acids from the comminuted oilseed sample;
    c) adding to said first mixture a Reagent B to form a second mixture, wherein Reagent B reextracts said free fatty acids from said first extract and comprises a strong acid and an inorganic salt in water;
    d) agitating said second mixture to produce a lower phase, a middle phase, and an upper hydrocarbon phase, thus taking up said free fatty acids into said upper hydrocarbon phase;
    e) removing an aliquot from said upper hydrocarbon phase containing said free fatty acids; and
    f) determining the acid value of said comminuted oilseed sample from said aliquot.

2. A method according to claim 1, wherein the alcohol in Reagent A is isopropanol at a concentration of about 50 to 65 vol-%.

3. A method according to claim 1, wherein the hydrocarbon in Reagent A is heptane at a concentration of about 28 to 48 vol-%.

4. A method according to claim 1, wherein the tertiary amine in Reagent A is triethanolamine, at a concentration of about 0.05 to about 0.15M.

5. A method according to claim 1, wherein the strong acid in Reagent B comprises sulfuric acid at a concentration of about 0.5 to about 2.5M.

6. A method according to claim 1, wherein the inorganic salt in Reagent B is sodium sulfate at a concentration of about 1.3 to about 1.5M.

7. A method for determination of an acid value of an oilseed which comprises:
    a) introducing a dried comminuted oilseed sample into a Reagent A comprising about 0.05 to 0.15M triethanolamine, about 1 to 7% by volume water, about 50 to 65% by volume isopropanol and about 28 to 48% by volume heptane to form a first mixture and agitating said first mixture for 1 to 2 minutes to thereby first extract free fatty acids and other acids from the comminuted oilseed sample;
    b) adding to said first mixture a Reagent B to form a second mixture, wherein Reagent B reextracts said free fatty acids from said first extract and comprises 0.5 to 2.5M sulfuric acid and about 1.3 to 1.5M sodium sulfate in water;
    c) agitating said second mixture for at least 5 minutes to produce a three phase mixture having a lower phase, a middle phase and an upper heptane phase, thus taking up said free fatty acids into said upper heptane phase;
    d) removing an aliquot from said upper heptane phase containing said free fatty acids; and
    e) determining the acid value of said comminuted oilseed sample from said aliquot.

8. The method according to claim 7, wherein the acid value is determined by titration.

9. The method according to claim 7, wherein the acid value is determined by a pH-metric technique.

* * * * *